United States Patent [19]

Torge

[11] Patent Number: 4,813,783
[45] Date of Patent: Mar. 21, 1989

[54] INTERFEROMETER SYSTEM FOR MAKING LENGTH OR ANGLE MEASUREMENTS

[75] Inventor: Reimund Torge, Aalen, Fed. Rep. of Germany

[73] Assignee: Carl-Zeiss-Stiftung, Heidenheim, Fed. Rep. of Germany

[21] Appl. No.: 116,376

[22] Filed: Nov. 3, 1987

[51] Int. Cl.$^4$ .............................................. G01B 9/02
[52] U.S. Cl. .................................... 356/358; 356/361
[58] Field of Search ........................ 356/358, 361, 363

[56] References Cited

U.S. PATENT DOCUMENTS 4,685,803  8/1987  Sommargren .................... 356/361

FOREIGN PATENT DOCUMENTS 3401900  1/1985  Fed. Rep. of Germany .

OTHER PUBLICATIONS

Kinder, "Ein Meter-Komparator für interferometrische Längeubestimmungen in Vakuum-Wellenlängen", Zeiss Wenkzeitschrift, vol. 43, pp. 3–11, 1962.

Grace, "Alaser Calibrator-Compensator to Upgrade the Long-Term Accuracy of a Commerical Laser Interferometer", Proc-SPIE, vol. 24, pp. 192-199, 1980.

Primary Examiner—Davis L. Willis
Assistant Examiner—Matthew W. Koren
Attorney, Agent, or Firm—Walter Ottesen

[57] ABSTRACT

The invention is directed to an interferometer which includes two interferometer systems and with which length measurement or angle measurement as well as index of refraction measurement can be conducted simultaneously. For this purpose, at least one component beam from the measuring arm of the one interferometer system and a component beam from a comparison arm of the other interferometer system are directed through an evacuable arrangement.

11 Claims, 3 Drawing Sheets

| Arrangement | Definition | Interferometer Arm | (V) (1) (11) (41) | (V) (2) (21) (43) | (M) (1) (12) (42) | (M) (2) (22) (44) |
|---|---|---|---|---|---|---|
| | | Interferometer System | | | | |
| | | Component Beam | | | | |
| | | Chamber | | | | |
| 1 | II | Beginning | v | v | v | v |
| | | End | l | v | v | l |
| 2 | | Beginning | v | v | v | v |
| | | End | v | l | l | v |
| 3 | III | Beginning | (l) | l | l | (l) |
| | | End | (l) | v | v | (l) |
| 4 | | Beginning | l | (l) | (l) | l |
| | | End | v | (l) | (l) | v |
| 5 | IV | Beginning | l | v | v | l |
| | | End | v | v | v | v |
| 6 | | Beginning | v | l | l | v |
| | | End | v | v | v | v |
| 7 | V | Beginning | (l) | v | v | (l) |
| | | End | (l) | l | l | (l) |
| 8 | | Beginning | v | (l) | (l) | v |
| | | End | l | (l) | (l) | l |

FIG. 5

INTERFEROMETER SYSTEM FOR MAKING LENGTH OR ANGLE MEASUREMENTS

FIELD OF THE INVENTION

The invention relates to an interferometer for making length or angle measurements which has a movable reflection element in a measuring arm and a stationary reflection element in a comparison arm. In addition to the interferometer system with component beams, the interferometer of the invention has a reference system or a second interferometric system with component beams and has an evacuable arrangement for determining the index of refraction of the air surrounding the interferometer.

BACKGROUND OF THE INVENTION

The index of refraction of the air surrounding the interferometer must be considered when making precise interferometric length or angle measurements since the index of refraction is included directly in the result of the measurement. German patent application DE-OS No. 34 01 900 discloses an interferometer with a reference system with which the index of refraction as well as a length or an angle can be measured simultaneously. For this purpose, an evacuable chamber is arranged in one component beam of the comparison arm and the reflection element of this component beam or of the other component beam is moved for length or angle measurements.

A disadvantage with this known interferometer is that the precision of the length measurement and of the index of refraction measurement is inadequate for very high requirements.

A publication entitled "Ein Meter-Komparator für interferometrische Längenbestimmungen in Vakuum-Wellenlänge" of Walter Kinder in the "Zeiss Werkzeitschrift" (Volume 43, 1962) pages 3 to 11, discloses a meter comparator for interferometric length determinations in vacuum wavelengths wherein the sensitivity of the determination of the index of refraction is doubled in that two chamber pairs are so utilized that two interferometric systems operate opposite to each other. The length measurement is achieved in a conventional manner with beams independent of the determination of the index of refraction.

SUMMARY OF THE INVENTION

It is an object of the invention to provide an interferometer wherein not only the index of refraction of air is determined with greater precision; instead, also the length and/or angle measurements are achieved with the highest greater precision possible. The interferometer shall nonetheless be as simple as possible in its configuration; that is, it is to have only the absolutely necessary number of component beams.

The above object is achieved with the interferometer according to the invention in that at least one component beam from the measuring arm of the one interferometer system and a component beam from a comparison arm of another interferometric system is guided through the evacuable arrangement.

In an advantageous embodiment of the invention, all four component beams are guided through the evacuable arrangement and the evacuable arrangement comprises two groups of chambers independent of each other. At the beginning of a measurement or measurement sequence, all evacuable chambers are devoid of air. At the end of first measurement and during all further measurements of a measuring sequence, those evacuable chambers are filled with the air surrounding the interferometer which are mounted in the measuring arm of the one interferometer system and in the comparison arm of the other interferometer system.

The possible arrangements of the evacuable chambers and their conditions at the beginning and at the end of the first measurement are discussed after the thorough description of an embodiment and are summarized in a table in the last figure of the drawing.

The arrangement of the evacuated chambers and of the chambers filled with air in the two interferometer systems correspond to the above-cited publication of Walter Kinder. However, and pursuant to the invention, the component beams running through the chambers are used simultaneously. for length or angle measurements with also the length or angle measurements being conducted with double the precision compared to conventional methods.

In a further advantageous embodiment of the invention, triple mirrors or triple prisms are utilized as reflection elements. Since in this case, the component beams are not reflected back into themselves and are instead returned in parallel displacement, up to eight evacuable chambers are used which are grouped into two sets independent of each other.

BRIEF DESCRIPTION OF THE DRAWINGS

The invention will now be described with reference to the drawings wherein:

FIG. 5 is a table providing an overview of all eight possibilities for the arrangement of the evacuable chambers and their conditions at the beginning and end of the measurements.

DESCRIPTION OF THE PREFERRED EMBODIMENTS OF THE INVENTION

Figure 1:
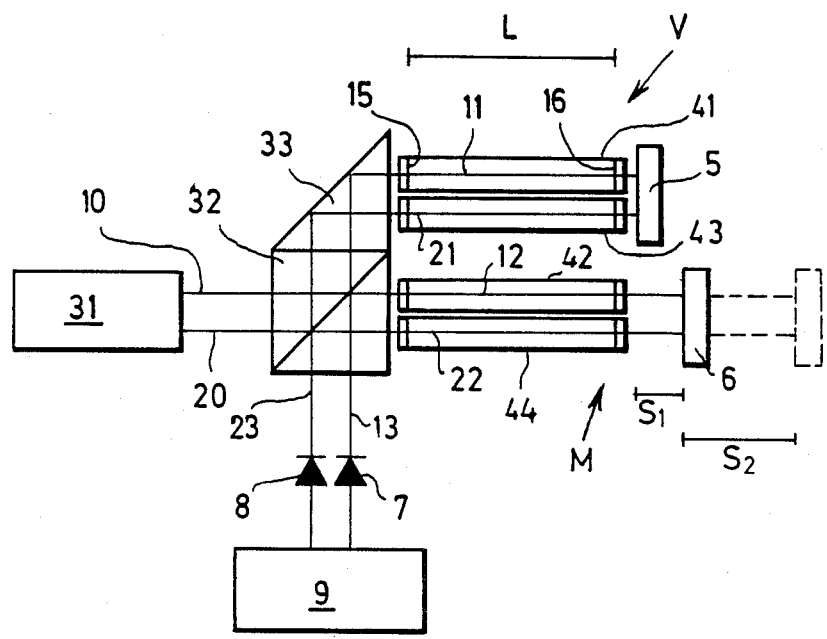
FIG. 1 is a schematic illustration of an embodiment of the invention in its basic configuration.

Referring to FIG. 1, two parallel beams (10 and 20) are generated by a suitable light source 31 such as a laser. The beam 10 belongs to the interferometer system 1 and is split into the two component beams 11 and 12 by the divider cube 32. After a deflection at prism 33, the component beam 11 passes through the comparison arm V having the evacuable chamber 41 and is again reflected back into the divider cube 32 by the mirror 5.

The component beam 12 passes through the measuring arm M having the evacuable chamber 42 and is likewise reflected back to the divider cube 32 by means of the mirror 6. At divider cube 32, the component beam 12 is united with the component beam 11 to form a common beam 13 with interferences arising because of the superposing of the two component beams which is detected with appropriate measurement techniques by means of the receiver 7 and is processed by means of the evaluation unit 9.

The parallel beam 20 belongs to interferometer system 2 and is split into the component beams (21 and 22)

in the divider cube 32. The component beam 21 runs parallel to the component beam 11 via the deflection prism 33 and through the comparison arm V having the evacuable chamber 43 and then to the mirror 5 and is likewise reflected back by the mirror 5 to the divider cube 32. The component beam 22 runs parallel to the component beam 12 and through the measuring arm M with the evacuable chamber 44 and is reflected back by the mirror 6 into the divider cube 32 where the component beam 22 is united with the component beam 21 to form a common beam 23 with interferences likewise occurring between the two component beams which are detected with appropriate measuring techniques by means of the receiver 8 and processed by means of the evaluation unit 9.

For the following embodiments, it is assumed that all windows (15, 16) of the evacuable chambers (41, 42, 43, 44) have the same thickness. Furthermore, the length of the component beams (11, 12, 21, 22) is computed starting at the exit of the divider cube 32 or from the deflection prism 33 and its return entry into the latter since the different paths in these component parts would mutually eliminate each other in the course of the computation. The following definitions are now provided:

(11),(12): Component beams of interferometer system 1
(21),(22): Component beams of interferometer system 2
A: Air path of the component beams 12 and 22 in measuring arm M without evacuable chambers (42 and 44)
R: Air path of the component beams 11 and 21 in the comparison arm V without evacuable. chambers 41 and 43
n: Index of refraction of air
L: Length of the evacuable chambers
$h_{ij}$: Ordinal number of the interferences in condition i of the interferometer system j
w: Vacuum wave number In the starting condition of the interferometer, all four chambers (41, 42, 43, 44) are evacuated and the index of refraction of the air surrounding the interferometer is $n_0$. The optical path lengths then are:

in component beam 11: $Rn_0+L$ /1a/ in component beam 12: $An_0+L$ /1b/ in component beam 21: $Rn_0+L$ /1c/ in component beam 22: $An_0+L$ /1d/

In this way, the following is obtained for the ordinal numbers (number of interference)

in the interferometer system 1: $h_{01}=2wn_0(A-R)$ /2a/ in the interferometer system 2: $h_{02}=2wn_0(A-R)$ /2b/

For the difference of the ordinal numbers, the following output condition applies:

$h_{01}-h_{02}=0$ /3/

For the first measurement, the chambers 41 and 44 are filled with air. At the same time, the mirror 6 can be displaced about $S_1$ to the reference point of the following measurement (when the mirror $S_1$ does not already stand there), that is, its drift with respect to the output condition can be determined. The index of refraction of the air surrounding the interferometer is now $n_1$. The optical path lengths amount then to the following:

in component beam 11: $Rn_1+Ln_1$ /4a/ in component beam 12: $An_1+L+S_1n_1$ /4b/ in component beam 21: $Rn_1+L$ /4c/ in component beam 22: $An_1+Ln_1+S_1n_1$ /4d/

This leads to the ordinal numbers which are provided for interferometer systems 1 and 2:

in the interferometer system 1:

$h_{11}=2w[(A-R)n_1-L(n_1-1)+S_1n_1]$ /5a/ in the interferometer system 2:

$h_{12}=2w[(A-R)n_1+L(n_1-1)+S_1n_1]$ /5b/

The following results as the difference of the ordinal numbers with respect to the output condition:

in the interferometer system 1:

$h_{11}-h_{01}=2w[(A-R)(n_1-n_0)-L(n_1-1)+S_1n_1]$ /6a/ and, for the interferometer system 2:

$h_{12}-h_{02}=2w[(A-R)(n_1-n_0)+L(n_1-1)+S_1n_1]$ /6b/

The subtraction of the changes of both interferometer systems results in the index of refraction $n_1$:

$h_{12}-h_{02}-h_{11}+h_{01}=4wL(n_1-1)$ /7/

With equation /7/, the addition changes of both interferometer systems results in the displacement $S_1$ of the mirror 6 (and a noise term)

$h_{11}-h_{01}+h_{12}-h_{02}=4wS_1n_1+4w(A-R)(n_1-n_0)$ /8/

The geometric asymmetry $A-R$ of the interferometer can be measured by conventional means or with the interferometer itself without an index of refraction correction because for an index of refraction change $n_1-n_0=10^{-6}$ (corresponding to a temperature change of 1 K), an error of 1 mm results for $A-R$ first in a noise term of $10^{-3}$ μm which can be neglected.

For the second measurement, the mirror 6 is displaced by the distance $S_2$. The index of refraction of the air surrounding the interferometer and in the chambers 41 and 44 has changed to $n_2$. The optical path lengths then are:

in component beam 11: $Rn_2+Ln_2$ /9a/ in component beam 12: $An_2+L+S_1n_2+S_2n_2$ /9b/ in component beam 21: $Rn_2+L$ /9c/ in component beam 22: $An_2+Ln_2+S_1n_2+S_2n_2$ /9d/

From the foregoing, the following results for the ordinal numbers in interferometer systems 1 and 2 as follows:
in the interferometric system 1:

$h_{21}=2w[(A-R)n_2-L(n_2-1)+S_2n_2+S_1n_2]$ /10a/ in the interferometric system 2:

$$h_{22} = 2w[(A-R)n_2 + L(n_2-n_1) + S_2 n_2 + S_1 n_2] \quad /10b/$$

As the difference of the ordinal numbers with respect to the previous condition, there results:
for interferometric system 1:

$$h_{21} - h_{11} = 2w[(A-R)(n_2-n_1) - L(n_2-n_1) + S_2 n_2 + S_1(n_2-n_1)] \quad /11a/$$

for interferometric system 2:

$$h_{22} - h_{12} = 2w[(A-R)(n_2-n_1) - L(n_2-n_1) + S_2 n_2 + S_1(n_2-n_1)] \quad /11b/$$

The subtraction of the changes of both interferometer systems results in a change of the index of refraction $$h_{22} - h_{12} + h_{21} - h_{11} = 4wL(n_2-n_1) \quad /12/$$

The addition of the changes of both interferometer systems results in the displacement $S_2$ of mirror 6 with the equations /7/, /8/ and /12/:

$$h_{21} - h_{11} + h_{22} - h_{12} = 4wS_2 n_2 + 4wS_1(n_2-n_1) + 4w(A-R)(n_2-n_1) \quad /13/$$

For the noise term caused by the geometric asymmetry $(A-R)$, what was stated with respect to equation /8/ applies. The product $S_1(n_2-n_1)$ is negligible for small changes of $S_1$.

For all following measurements of a measurement sequence, the evaluation is performed in correspondence to the last description above.

For the measurements, the mirror 6 should first be so adjusted that the interferometer is geometrically adjusted, that is, $A=R$. In this way, negligible noise terms and optimal freedom from drift are obtained.

From the equations /7/ and /12/, the index of refraction is obtained with double the precision compared to conventional interferometer. Likewise, the displacement $S_2$ of mirror 6 is obtained from equation /13/ with double precision.

From the equations (/6a/ and /6b/) and (/11a/ and /11b/), two values of the index of refraction (double measurement) are obtained with the equations /8/ and /13/. In this way, it is possible to obtain the dispersion of the method from double measurements and to secure the measuring result against error by a miscount. From equations (/11a/ and /11b/), two values are likewise obtained with the equations /8/ and /12/ for the displacement of the mirror $S_2$ with the above-mentioned advantages of double measurement.

FIG. 1 is a schematic illustration of a basic configuration of the interferometer system according to the invention. Each of the individual receivers 7 and 8 can be replaced with four receivers including a quarter-wave plate ($\lambda$/4-plate) and polarizers whereby the phase position can be traced. Furthermore, in lieu of the planar mirrors 5 and 6, triple mirrors or triple prisms 5a and 6a can be utilized which have the advantage that the reflected beam always returns parallel to the incident beam. However, with such triple prisms, the beam paths can no longer be clearly seen so that in FIG. 2 only a plan view of the triple prism with a section through the component beams and evacuable chambers is shown. The triple prism 5a replaces the mirror 5 and the triple prism 6a replaces the mirror 6. In the case of triple mirrors or triple prisms, the component beams are not reflected into themselves; instead, they return at a position which is displaced laterally and in elevation.

Figure 2:
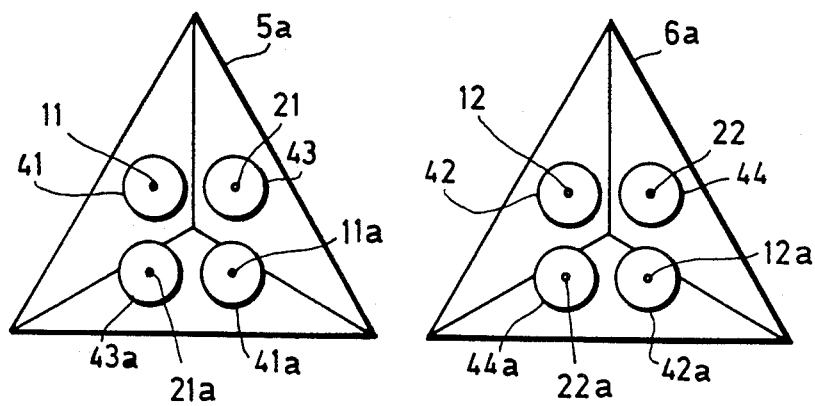
FIG. 2 is a schematic of an arrangement of the evacuable chambers with respect to two triple prisms.

The component beam 11 is reflected from a triple prism 5a in FIG. 2 as component beam 11a and the component beam 21 is reflected as component beam 21a. Correspondingly, the component beam 12 is reflected as 12a from the triple prism 6a and the component beam 22 is reflected as component beam 22a. As a consequence of this displacement of the component beams by means of their reflections on the triple prisms, it is purposeful to provide a total of eight evacuable chambers with the chambers (43, 43a, 42, 42a) being connected with each other and the chambers (41, 41a, 44, 44a) likewise being connected with each other. The chambers (43, 43a, 42, 42a) are always evacuated in the above-described example and the chambers (41, 41a, 44, 44a) are evacuated only at the beginning of a measuring sequence.

It is especially advantageous to use the known two-frequency method wherein the change of a length or an index of refraction is not obtained from the changes of the amplitude and is instead obtained from changes of the frequency. For this purpose, both frequencies are superposed and the double displacement of the superposing frequency is evaluated, the double displacement being brought about by the change of the length or of the index of refraction. The suitable configuration for this is shown in FIG. 3.

The laser 31 transmits two frequencies $f_1$ and $f_2$ in each of three beams 10, 20 and 30 which lie close to one another. In lieu of a laser with two frequencies, two lasers each having respective frequencies can be utilized which are different from one another. The unchanged superposing frequency arrives at the receiver 33 via the deflecting mirror 32 by means of the beam 30. The divider cube 2' is configured in a manner known per se such that the radiation with the one frequency goes into the component beam paths 11 and 21 and that the radiation with the other frequency goes into the component beam paths 12 and 22. Both frequencies then came together again in the beam paths 13 and 23. Frequency displacements occur in the component beam paths by means of changes of the optical path length as a consequence of the Doppler effect so that the superposed frequency also changes and deviates from that in the beam path 30. The integral of these differences over the time is a measure for the change of the length or of the index of refraction.

Each of the three receivers 7, 8 and 33 is connected to one of the three counters 35 to 37 for making the detection. The counters 35 to 37 count the light-dark changes of the superposing frequencies. In the subtractor 38, the difference between the two counters 35 and 37 is formed and in this way, the change in the measuring system with the beam paths 11 and 12 is detected. In subtractor 39, the difference between the two counters 35 and 36 is formed and the change in the reference system with the two beam paths 21 and 22 is detected. The evaluation unit 9' is connected to the subtractors 38 and 39. For this evaluation unit 9', the informations are available which were treated in FIG. 1. Further details about the frequency change by means of the Doppler effect can be taken, for example, from the publication of H. Kunzmann (Annals of the CIRP 28, 311, 1979).

Figure 3:
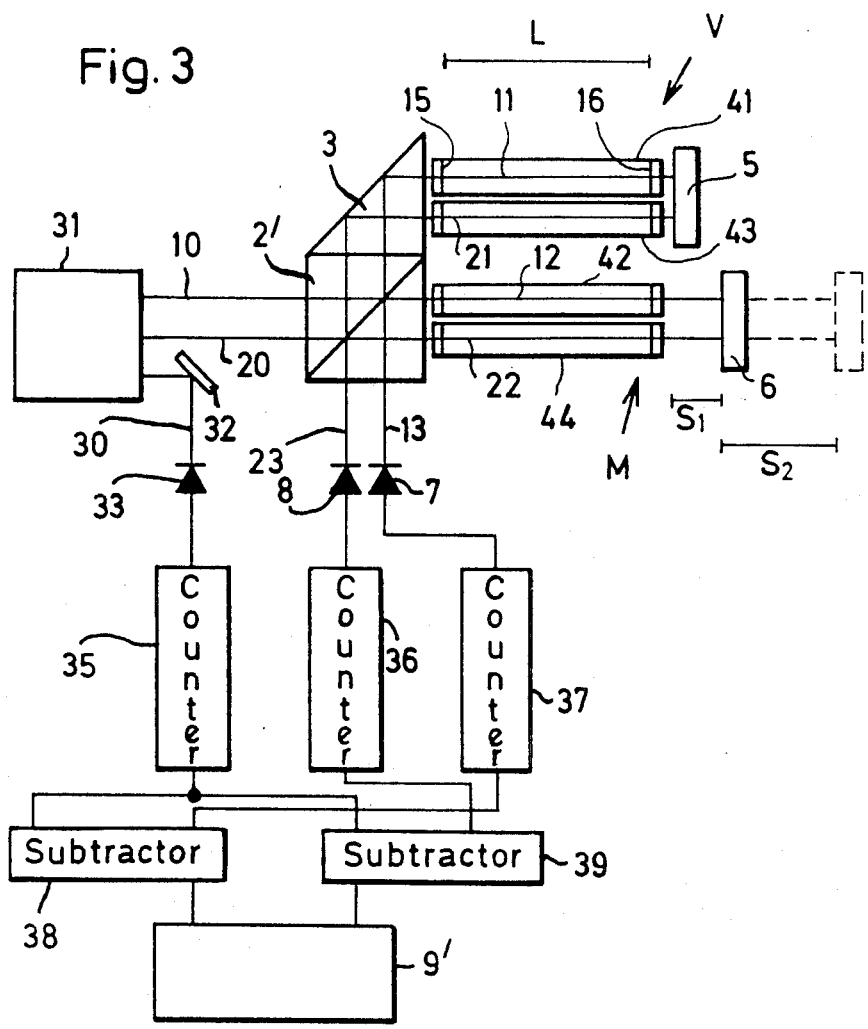
FIG. 3 is a schematic illustration of the configuration for the measurement according to the two-frequency method.
Figure 4:
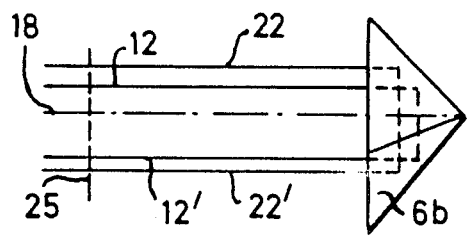
FIG. 4 is a schematic for an arrangement for angle measurement.

The interferometer configuration according to the invention can also be used for making angle measurements in that the mirror 6 in FIGS. 1 or 3 is replaced with a triple mirror 6b which is rotatable about the point 19 as shown schematically in FIG. 4. When the point 19 lies outside of the optical axis 18 of the triple mirror 6b a small rotation of the triple mirror 6b produces the effect that the incident beams 12 and 22 are further reflected as beams 12' and 22' parallel to the incident beams, and that, however, the optical paths from the plane 25 to the triple mirror 6b and back are changed. This change is detected by the interferometer and evaluated while taking into account the geometric arrangement.

In lieu of the interferometers of the Twyman type described with reference to FIGS. 1 and 3, also other correspondingly modified interferometers such as the Jamin type can be utilized.

The embodiment described in FIGS. 1 and 2 is one of a total of eight possibilities for the arrangement of the evacuable chambers and their conditions at the beginning and end of the measurements. An overview of all possibilities is provided in the table shown in FIG. 5. In the first of two columns in this table, the possibilities are listed as 1 to 8 and the number of the particular definition (II to V) of the invention corresponding thereto is listed. These definitions II to V are delineated below following a first definition I of the invention from which the remaining definitions are dependent.

Definition I: An interferometer for making length or angle measurements includes: a movable reflecting element 6 in a measuring arm M and a stationary reflecting element 5 in a comparison arm V; a first interferometer system 1 with component beams 11 and 12; a reference or second interferometer system 2 with component beams 21 and 22; and, an evacuable arrangement for determining the index of refraction of the air surrounding the interferometer. At least one component beam 12 from the measuring arm M of the first interferometer system and one component beam 21 from the comparison arm V of the second interferometer system are directed through the evacuable arrangement (42, 43).

Definition II: All four component beams (11, 12, 21, 22) are directed through the evacuable arrangement which includes two systems independent of each other, the systems having the chambers (41, 44 and 42, 43). At the beginning of a measurement or measuring sequence all of the evacuable chambers (41, 42, 43, 44) are devoid of air and at the end of the measurement and during all further measurements of a measuring sequence, those evacuable chambers (41, 44) which are arranged in the first interferometer system 2 in the measuring arm M and which are arranged in the second interferometer system 1 in the comparison arm V are filled with the ambient air of the interferometer.

Definition III: At least one component beam 12 from the measuring arm M of the first interferometer system and one component beam 21 from the comparison arm V of the second interferometer system are directed through the evacuable arrangement (42, 43). At the beginning of a measurement or measurement sequence, the evacuable arrangement is filled with the ambient air of the interferometer and, after the first measurement and during all further measurements of a measurement sequence, the evacuable arrangement is devoid of air.

Definition IV: All four component beams (11, 12, 21, 22) are directed through the evacuable arrangement which includes two systems independent of each other, the systems having the chambers (41, 44 and 42, 43). At the beginning of a measurement or measuring sequence, those evacuable chambers (41, 44) which are arranged in the one interferometer system 2 in the measuring arm M and the other interferometer system 1 in the comparison arm V are filled with the ambient air of the interferometer and at the end of the measurement and during all further measurements of a measuring sequence, all evacuable chambers (41, 42, 43, 44) are devoid of air.

Definition V: At least one component beam 12 from the measuring arm M of the first interferometer system and one component beam 21 from the comparison arm V of the second interferometer system are directed through the evacuable arrangement (42, 43). At the beginning of a measurement or measuring sequence, the evacuable arrangement (42, 43) is devoid of air and at the end of the measurement and during all further measurements, the evacuable arrangement is filled with the ambient air of the interferometer.

In the columns on the right side of the vertical partition line in the table of FIG. 5, the interferometer arms, interferometer systems, component beams and chambers are listed as they are designated in FIG. 1. The designation "beginning" means the beginning of a measurement or measuring sequence. The designation "end" means the end of the first measurement; this condition remains during all further measurements of a measuring sequence.

In the table of FIG. 5, the letters v, l and (l) mean the following:

v: the chamber is evacuated, l: means the chamber is filled with the ambient air of the interferometer, (l): the chamber is continuously filled with the ambient air of the interferometer and is therefore superfluous.

Arrangement 1 in the table is the example which is explained in detail in the foregoing. For the arrangement 2, those chambers which are filled with air belong respectively to other interferometer systems. The arrangements 1 and 2 are contained in definition II. For arrangement 2, it is understood that the evaluation is performed in correspondence with equations /1/ to /13/ and that there are no major differences.

In arrangements 3 and 4, all chambers are filled with air at the beginning and two chambers are evacuated at the end of the first measurement. Therefore, only two chambers are needed which can be taken together as a single evacuable arrangement through which the component beams (21 and 12) and (11 and 22) pass. Also in the case of the use of triple mirrors or triple prisms, the assembly of the evacuable arrangement in this case is substantially simpler than with the arrangements 1 and 2. This advantage of arrangements 3 and 4 must be contrasted with the disadvantage that the evacuation of chambers generally takes longer than the ventilation and that therefore more time for the first length measurement is needed than with arrangements 1 and 2.

The arrangements 5 to 8 correspond to arrangements 1 to 4 up to the difference that evacuation and ventilation are interchanged. With these arrangements, the change of the index of refraction during the first length measurement is not detected. They are therefore less advantageous; however, they can always be utilized when no or only small changes of the index of refraction are to be expected.

With all of the arrangements, the evaluation is performed in the same way as in the evaluation which was detailed completely above for arrangement 1. With all of the arrangements, the measurement of the index of refraction as well as the measurement of length or the measurement of angle is performed with double the precision compared to conventional arrangements.

The interferometer in all cases can be surrounded with a gas rather than air which then is used for filling the evacuable chambers. In addition, for further increasing the precision, the measurement method of the different arrangements can be conducted alternately one after the other, for example, the measurement method of arrangements 1 and 5.

It is understood that the foregoing description is that of the preferred embodiments of the invention and that various changes and modifications may be made thereto without departing from the spirit and scope of the invention as defined in the appended claims.

What is claimed is:

1. An interferometer for making length or angle measurements comprising:
   an evacuable arrangement for determining the index of refraction of air surrounding the interferometer, the evacuable arrangement including first and second evacuable chamber means;
   a first interferometer system for generating first and second component beams, said first interferometer system including a first comparison arm and a first measuring arm;
   said first measuring arm including said first evacuable chamber means and a movable reflection means mounted adjacent said first evacuable chamber means so as to be movable with respect to the latter;
   a second interferometer system for generating third and fourth component beams, said second interferometer system including a second comparison arm and a second measuring arm;
   said second comparison arm including said second evacuable chamber means and fixed reflection means fixedly mounted adjacent said second evacuable chamber means; and,
   optical means for directing said first and second component beams to said first comparison arm and said first measuring arm, respectively, and for directing said third and fourth component beams to said second comparison arm and said second measuring arm, respectively; and for directing said second component beam from said first measuring arm through said first evacuable chamber means and for directing said third component beam from said second comparison arm through said second evacuable chamber means.

2. The interferometer of claim 1, wherein said evacuating arrangement includes third and fourth evacuable chamber means;
   said first comparison arm including said third evacuable chamber means mounted adjacent fixed reflection means;
   said second measuring arm including said fourth evacuable means mounted adjacent said movable reflection means;
   said evacuable arrangement including two chamber systems independent of each other, the first chamber system including said third and fourth evacuable means and the second chamber system including said first and second evacuable means; and,
   said optical means directing all four of said component beams through said evacuable arrangement.

3. The interferometer of claim 1, wherein: said optical means directs said second component beam and said third component beam through said first evacuable chamber means and said second evacuable chamber means, respectively.

4. The interferometer of claim 1, wherein said evacuating arrangement includes third and fourth evacuable chamber means;
   said first comparison arm including said third evacuable chamber means mounted adjacent fixed reflection means;
   said second measuring arm including said fourth evacuable means mounted adjacent said movable reflection means;
   said evacauble arrangement including two chamber systems independent of each other, the first chamber system including said first and second evacuable means and the second chamber system including said third and fourth evacuable means; and,
   said optical means directing all four of said component beams through said evacuating arrangement.

5. The interferometer of claim 1, wherein: said optical means directs said second component beam and said third component beam through said first evacuable chamber means and said second evacuable chamber means, respectively.

6. The interferometer of claim 1, said movable reflection means and said fixed reflection means being a movable triple reflection means and a fixed triple reflection means, respectively.

7. The interferometer of claim 6, said triple reflection means being a triple reflecting mirror.

8. The interferometer of claim 6, said triple reflection means being a triple prism.

9. The interferometer of claim 6, wherein said evacuating arrangement includes third and fourth evacuable chamber means;
   said first comparison arm including said third evacuable chamber means mounted adjacent fixed reflection means;
   said second measuring arm including said fourth evacuable means mounted adjacent said movable reflection means;
   said four component beams being directed into selected ones of said evacuable chambers by said optical means and being reflected at said triple reflection means in four reflected component beams, respectively; and,
   said evacuable arrangement including four additional evacuable means corresponding to respective ones of said four reflected component beams.

10. The interferometer of claim 6, one of said triple reflection means having an optical axis and being rotatable about a point displaced from said optical axis for making angle measurements.

11. The interferometer of claim 1, said optical means including:
    a light source for issuing light having first and second frequencies;
    optical directing means for directing said first frequency into said first and second comparison arms so as to pass along the respective component beam paths thereof and for directing said second frequency into said first and second measuring arms so as to pass along the respective component beam paths thereof;
    said optical directing means also joining said frequencies after the latter have passed along said component beam paths; and,
    said interferometer further including counter means and subtraction means for receiving the joined frequencies and for evaluating the light-dark exchange of the superposing frequencies.

* * * * *

UNITED STATES PATENT AND TRADEMARK OFFICE
CERTIFICATE OF CORRECTION

PATENT NO. : 4,813,783
DATED : March 21, 1989
INVENTOR(S) : Reimund Torge

It is certified that error appears in the above-identified patent and that said Letters Patent is hereby corrected as shown below:

In column 2, line 1: insert -- the -- between "of" and "first".

In column 2, line 17: delete "simultaneously." and substitute -- simultaneously -- therefor.

In column 3, line 32: delete "evacuable." and substitute -- evacuable -- therefor.

In column 4, delete the formula corresponding to /6b/ and substitute:
-- $h_{12} - h_{02} = 2w[(A - R)(n_1 - n_0) + L(n_1 - 1) + S_1 n_1]$ --
therefor.

UNITED STATES PATENT AND TRADEMARK OFFICE
CERTIFICATE OF CORRECTION

PATENT NO. : 4,813,783
DATED : March 21, 1989
INVENTOR(S) : Reimund Torge

It is certified that error appears in the above-identified patent and that said Letters Patent is hereby corrected as shown below:

In column 5, delete the formula corresponding to /11a/ and substitute:

-- $h_{21} - h_{11} = 2w[(A - R)(n_2 - n_1) - L(n_2 - n_1) + S_2 n_2 + S_1(n_2 - n_1)]$ -- therefor.

In column 5, delete the formula corresponding to /11b/ and substitute:

-- $h_{22} - h_{12} = 2w[(A - R)(n_2 - n_1) - L(n_2 - n_1) + S_2 n_2 + S_1(n_2 - n_1)]$ -- therefor.

UNITED STATES PATENT AND TRADEMARK OFFICE
CERTIFICATE OF CORRECTION

PATENT NO. : 4,813,783
DATED : March 21, 1989
INVENTOR(S) : Reimund Torge

It is certified that error appears in the above-identified patent and that said Letters Patent is hereby corrected as shown below:

In column 5, delete the formula corresponding to /13/ and substitute:

-- $h_{21} - h_{11} + h_{22} - h_{12} = 4wS_2 n_2 + 4wS_1 (n_2 - n_1) + 4w(A - R)(n_2 - n_1)$ -- therefor.

In column 5, line 41: delete "interferometer" and substitute -- interferometry -- therefor.

In column 5, line 60: delete "6a" and substitute -- 6b -- therefor.

UNITED STATES PATENT AND TRADEMARK OFFICE
CERTIFICATE OF CORRECTION

PATENT NO. : 4,813,783
DATED : March 21, 1989
INVENTOR(S) : Reimund Torge

It is certified that error appears in the above-identified patent and that said Letters Patent is hereby corrected as shown below:

In column 6, line 41: delete "came" and substitute -- come -- therefor.

In column 8, line 40: delete "/1/" and substitute -- /1a/ -- therefor.

In column 10, line 12: delete "evacauble" and substitute -- evacuable -- therefor.

Signed and Sealed this

Twenty-seventh Day of March, 1990

Attest:

JEFFREY M. SAMUELS

*Attesting Officer*  *Acting Commissioner of Patents and Trademarks*